(12) United States Patent
Peyman

(10) Patent No.: US 6,936,043 B2
(45) Date of Patent: *Aug. 30, 2005

(54) METHOD TO TREAT AGE-RELATED MACULAR DEGENERATION

(75) Inventor: Gholam A. Peyman, New Orleans, LA (US)

(73) Assignee: Minu, LLC, Pittsboro, NC (US)

( * ) Notice: Subject to any disclaimer, the term of this patent is extended or adjusted under 35 U.S.C. 154(b) by 290 days.

This patent is subject to a terminal disclaimer.

(21) Appl. No.: 10/008,296

(22) Filed: Nov. 13, 2001

(65) Prior Publication Data

US 2003/0093064 A1 May 15, 2003

(51) Int. Cl.[7] ............................................. A61B 18/18
(52) U.S. Cl. ................................ 606/4; 606/5; 607/89; 128/898
(58) Field of Search ..................... 606/4–6; 128/898; 607/88, 89

(56) References Cited

U.S. PATENT DOCUMENTS

| | | | | |
|---|---|---|---|---|
| 5,633,275 | A | * | 5/1997 | Mori et al. .................. 514/410 |
| 5,935,942 | A | * | 8/1999 | Zeimer .......................... 514/63 |
| 6,162,242 | A | * | 12/2000 | Peyman ........................ 607/88 |
| 6,524,330 | B1 | * | 2/2003 | Khoobehi et al. ............. 607/89 |
| 6,607,522 | B1 | * | 8/2003 | Hamblin et al. ................ 606/8 |
| 2002/0165525 | A1 | * | 11/2002 | Nakamura ...................... 606/4 |
| 2003/0171320 | A1 | * | 9/2003 | Guyer .......................... 514/44 |
| 2004/0002694 | A1 | * | 1/2004 | Pawlowski et al. ............ 606/4 |

OTHER PUBLICATIONS

The Choroidal Neovascularization Prevention Trail Group "Laser Treatment in Eyes with Large Drusen: Short–term Effects Seen in a Pilot randomized Clinical Trial," Arch. Ophthalmol., Feb., 2001; 119: 198–207.*

Exhibit A "The latest research on photodynamic therapy for macular degeneration," American Federation for Aging Research, Apr. 3, 2003, www.infoaging.org/d–macu–6–r–photodynamic.html.*

The Choroidal Neovascularization Prevention Trail Group "Laser Treatment in Eyes with Large Drusen: Short–term Effects See in a Pilot randomized Clinical Trial," Arch. Ophthalmol., Feb., 2001; 119: 198–207.*

Bressler, N.M.: Photodynamic Therapy of Subfoveal Choroidal Neovascularization in Age–related Macular Degeneration with Verteporfin: One–year Results of 2 Randomized Clinical Trials—TAP Report 1, *Ophthlmol.* 1999; 117: 1329–45.

Bressler, N.M.: Photodynamic Therapy of Subfoveal Choroidal Neovascularization in Age–Related Macular Degeneration with Verteporfin: Two–year Results of 2 Randomized Clinical Trials—TAP Report 2, *Ophthalmol.* 2001; 119: 198–207.

(Continued)

*Primary Examiner*—A. Farah
(74) *Attorney, Agent, or Firm*—Wood, Herron & Evans, L.L.P.

(57) ABSTRACT

Age-related macular degeneration (AMD) results in the formation of new blood vessels in the eye. The walls of these vessels leak fluid, which causes scarring in the surrounding tissue, resulting in reduced vision or loss of vision. Photodynamic therapy (PDT) alone has been used to treat AMD, but many retreatments are needed, which cause further damage to the already diseased area. Laser treatment to coagulate the fluid actually causes additional new vessels to form. However, the inventive method of treating patients with both PDT and laser coagulation surprisingly either improved vision, or prevented further loss of vision. Moreover, the combined treatment eliminated the need for retreatment, and did not generate new vessel growth. Laser coagulation and PDT may be administered within the same treatment session or either may be administered first and the other may be administered within ninety days.

26 Claims, 1 Drawing Sheet

OTHER PUBLICATIONS

The Choroidal Neovascularization Prevention Trial Research Group: Laser Treatment in Eyes with Large Drusen: Short-term Effects Seen in a Pilot Randomized Clinical Trial, *Arch. Ophthalmol.*, Feb., 2001; 119: 198–207.

Verteporfin in Photodynamic Therapy Study Group: Verteporfin Therapy of Subfoveal Choroidal Neovascularization in Age–related Macular Degeneration: Two–year Results of a Randomized Clinical Trial Including Lesions with Occult with no Classic Choroidal Neovascularization—Verteporfin in Photodynamic Therapy Report 2, *Am. Jour. of Ophthal.*, May, 2001; 131: 541–560.

Poster, "Combined Verteporfin Ocular Photodynamic Therapy with Macular Scatter Photocoagulation for Occult Subfoveal Neovascularization in ARMD", Gholam Peyman, et al., Retina Congress, Sep. 28–Oct. 2, 2002.

Peyman, et al., *Verteporfin Ocular Photodynamic Therapy Combined with Macular Scatter Photocoagulation of Occult or Predominantly Occult Subfoveal Neovascularization in Age–Related Macular Degeneration: A Follow Up*, Association for Research in Vision and Opthalmology (ARVO), Abstract, presented May 8, 2003 at the ARVO Conference, Poster Session Program No./Board No. 4999–B658.

Poster, *Verteporfin Ocular Photodynamic Therapy Combined with Macular Scatter Photocoagulation of Occult or Predominantly Occult Subfoveal Neovascularization in Age–Related Macular Degeneration: A Follow Up*, Peyman, et al., Association for Research in Vision and Ophthalmology (ARVO) Conference, May 4–9, 2003; presented May 8, 2003, Poster Session Program No./Board No. 4999–B658.

\* cited by examiner

METHOD TO TREAT AGE-RELATED MACULAR DEGENERATION

FIELD OF THE INVENTION

The invention is directed generally to an ophthalmological process, and more specifically to a process to improve, maintain, or reduce loss of visual acuity in a patient having or at risk for developing macular degeneration.

BACKGROUND OF THE INVENTION

In the mammalian eye, macular degeneration (also called age related macular degeneration, AMD) is a pathological condition that is the most common cause of legal blindness among individuals over the age of 60, with an incidence ranging from 11% to 18.5% in individuals over the age of 85. In the United States, AMD affects roughly 3.6 million individuals, with over 200,000 new cases developing annually.

One type of AMD results in proliferation of new blood vessels in the subretinal area, typically the choroid. In the normal retina, both the large blood vessels and the capillaries have intact vessel walls. In the normal choroid, the large vessels have intact vessel walls, but the capillaries have fenestrations or openings in their walls. In patients with AMD, new blood vessels proliferate from the choriocapillaries through defects in Bruch's membrane beneath or on top of retinal pigment epithelium (RPE), and form vascular membranes. The resulting choroidal neovascularizations (new vessels in the choroid) occur in about 8–10% of all patients with AMD, and are also seen in patients with pathologic myopia and presumed ocular histoplasmosis syndrome, as well as other idiopathic conditions.

While the presence of the new vessels themselves is not problematic, any endogenous or exogenous fluid contained in these vessels (for example, blood, serous fluid, solubilized drug, etc.) will leak outside of the vessels and into the surrounding spaces. This accumulation of fluid can result in serous and hemorrhagic detachment of the RPE and neurosensory retina, and can lead to scarring in this area (fibrous deform scarring), resulting in decreased vision or even loss of vision. Thus, it is the fluid leakage from these new vessels in this type of AMD, called neovascular, exudative, or occult AMD, that is the cause of the resulting visual impairment.

Another type of AMD occurs less commonly and is due to dead RPE cells; this is termed atrophic AMD. In either type of AMD, without treatment, many of the affected individuals will become legally blind.

Patients with an early stage of AMD can be diagnosed in an examination by the presence of abnormal clumps of pigments in the eye. Accumulated dead outer segments of photoreceptor cells under the RPE is termed drusen. Hyaline excrescences that are located in Bruch's membrane (lamina basalis choroidea) also form. The presence of large, soft drusen in the eye indicates a pre-stage of exudative AMD, and places patients at higher-than-average risk for developing neovascularizations, especially if one eye is already affected.

To date, there are no known specific measures to prevent the occurrence of AMD. Nutritional therapies using antioxidants and zinc have been tried. There is one report (*Ophthalmology* 105:11–23, 1998) of a clinical trial using lasers to prophylactically treat patients showing abnormal pigment in both eyes (bilateral drusen).

For patients already diagnosed with AMD in one or both eyes, treatment involves targeting light (phototherapy) to the macular area containing the nascent defective blood vessels to inhibit or impair their function. One type of phototherapy is photodynamic therapy (PDT). In PDT, a photosensitive agent is administered into the vessels of a patient, then the agent is activated at the target site of the new vessels (the macula) by directing low energy light from a laser specifically to this area. The activated agent generates free radicals and other activated chemical species which destabilize and destroy the new vessels.

PDT has been reported to be of some benefit to patients having AMD. For example, one study (*Arch. Ophthalmol.* 17:1329–1345, 1999) evaluated PDT in four hundred and two eyes from patients diagnosed with AMD in at least one eye. Treatment outcome was assessed by comparing the patient's ability to accurately read a conventional vision chart (one having about five letters per line) pre-treatment and post-treatment. At twelve months post-PDT, 61% of the eyes (246/402) lost fewer than 15 letters (that is, the patient lost less than about three lines on a standard visual chart), while 46% of the eyes (96/207) from patients undergoing treatment with a placebo lost fewer than 15 letters ($p<0.001$). At twenty-four months post-PDT, the visual acuity and contrast sensitivity was sustained in patients receiving PDT. A significantly greater percentage of these patients (58%) lost fewer than 15 letters, compared to patients undergoing treatment with a placebo (38%). However, only 16% of the patients receiving PDT had improved vision, compared to 7% of the patients receiving a placebo.

Another type of phototherapy is photocoagulation therapy. In photocoagulation therapy, high energy light from a laser is directed specifically to the target site of the new vessels. The heat generated from the high energy laser coagulates the fluid in and around the new vessels. Laser photocoagulation is not a form of PDT; it is a separate treatment approach. It uses lateral transfer of heat, applied with a cautery-like method, to coagulate fluid within and surrounding the vessel, while PDT uses an activated photosensitive agent to generate active chemicals which damage or destroy the new vessels.

While either PDT or laser photocoagulation therapy is separately used to treat patients with AMD, neither is without drawbacks. A problem with PDT is that its effects are transient; patients receiving PDT must be retreated about every three months. Furthermore, the patients require at least five retreatments within the first two years merely to stabilize their condition, and before any therapeutic effect occurs. These cumulative treatments damage the retina, further reducing the patient's visual acuity.

One drawback of laser photocoagulation is that it is non-selective, and does not target only the new blood vessels. It must therefore be administered so that only the lesions are targeted, and the unaffected surrounding tissues are undamaged. However, in about half of the patients with AMD, the new vessels are located in the subfoveal area, which is difficult or impossible to target with laser coagulation without damaging the sensory retina. Another drawback is that photocoagulation treatment is not permanent and recurrence rates for new vessel production are high, reaching 39–76%, usually within the first two years. However, repeated treatments can actually induce the growth of new vessels and membranes (subretinal neovascular membranes and recurrent choroidal neovascularizations) at the site of the treatment. Repeated treatments may also irreversibly damage unaffected areas of the retina, including the neurosensory retina and RPE. Thus, the treatment itself may result in the patient having further reduced vision over a period of time. Specifically, some patients undergoing photocoagulation therapy develop scotoma, which is an area of depressed vision within the visual field, surrounded by an area of less depressed or of normal vision.

Methods to further refine the treatment of AMD to reduce or eliminate the above-described problems are therefore needed. Methods to prevent or delay the onset of AMD, and methods to maintain visual acuity and prevent further loss of vision in patients with AMD, are also needed.

SUMMARY OF THE INVENTION

The invention is directed to a method to prevent, alleviate, or delay the onset of AMD in a patient by administering photodynamic therapy (PDT) simultaneously or concomitantly with laser coagulation therapy. The invention is also directed to a method to prevent the progression of AMD, and to reduce further loss of vision in a patient having AMD, by administering PDT simultaneously or concomitantly with laser coagulation therapy. Surprisingly and beneficially, with the combined therapies, there is no need for retreatment of patients, as is required when PDT is separately administered, and there are no laser-induced neovascularizations, as occur when laser coagulation therapy is separately administered. Another benefit of the invention is that visual acuity is either maintained or is improved, without further loss of vision. The inventive therapy may be administered in any sequence, that is, laser coagulation therapy may be administered before or after PDT, or simultaneously with PDT. The invention can be used for both exudative and atrophic types of AMD.

An effective amount of a photosensitive agent for PDT is administered to a patient. The photosensitive agent is activated by low energy light that is directed to the neovascular target site using a laser (non-thermal laser). The photoactivated agent produces activated oxygen species, such as hydroxyl radicals and other radicals, that damage the new vessels, and may occlude the vessels. High energy light sufficient to create heat is also directed to the neovascular target site using a laser (thermal laser), resulting in coagulation of the fluid within and surrounding the new vessels. Either PDT or laser coagulation may be performed first, and the time between the two therapies may be within a few minutes, within a few hours, within a few days, or up to ninety days. PDT and laser coagulation may also be performed essentially simultaneously.

The invention is also directed to a method to improve visual acuity, and/or prevent further loss of vision in a patient already diagnosed with AMD, using the method described above.

The invention is further directed to a method to reduce the recurrence of new vessels in an eye of a patient having undergone PDT to treat AMD by further treating the patient with laser coagulation therapy concomitantly with the PDT in progress. The laser coagulation therapy may be administered within a few minutes of PDT, with a few hours of PDT, within 24 hours of PDT, or even ninety days after PDT. Alternatively, the laser coagulation therapy may have been administered, and thereafter the patient's standard PDT may be administered within a few minutes, within a few hours, within 24 hours, or up to ninety days after laser coagulation therapy.

The invention is also directed to a method to reduce the recurrence of new vessels in an eye of a patient having undergone laser coagulation therapy for AMD by further treating the patient with PDT concomitantly with laser coagulation therapy in progress, as described above. Alternatively, PDT may be administered first, and then the patient's standard laser coagulation laser therapy may be administered.

The invention is additionally directed to a method to minimize photosensitivity of a patient undergoing or having undergone PDT by administering the photosensitive agent to vessels of the patient and activating the agent with a low energy light, then treating the patient with plasmaphoresis to reduce the concentration of the agent in the patient's blood. In patients with AMD, plasmaphoresis is also beneficial in removing lipid components of the blood that may aggravate the disease, such as cholesterol and low density lipoproteins.

These and other embodiments of the invention will be further described in the following figures and detailed description.

DETAILED DESCRIPTION

Figure 1:
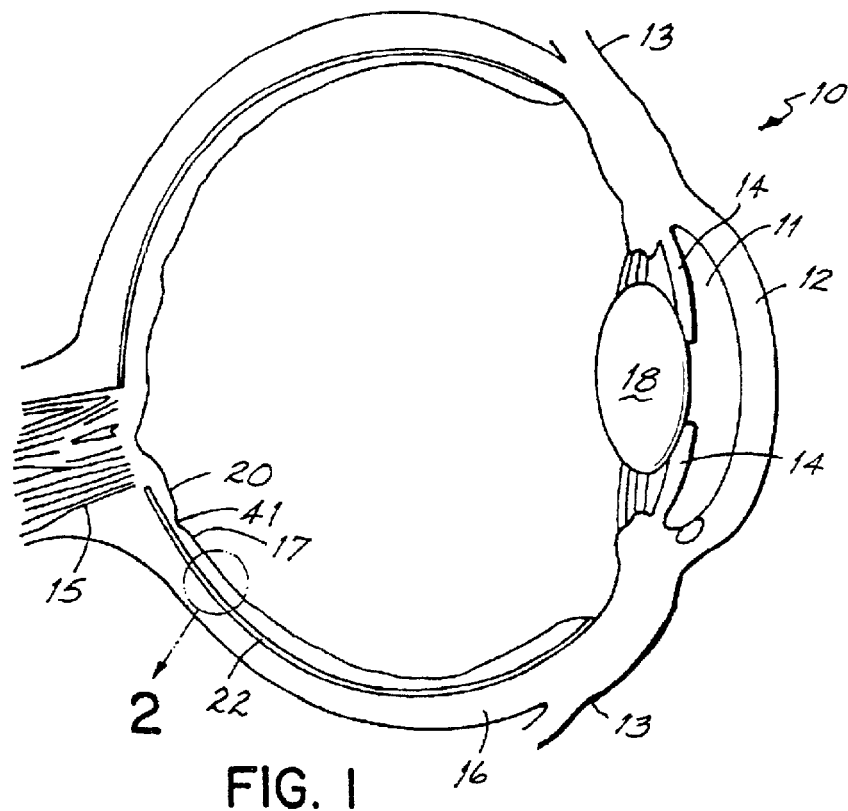
FIG. 1 is a schematic cross-sectional view of a mammalian eye.

With reference to FIG. 1, a mammalian eye 10 is shown. The locations of the anterior chamber 11, cornea 12, conjunctiva 13, iris 14, optic nerve 15, sclera 16, macula lutea 17, lens 18, retina 20 and choroid 22 are illustrated.

Figure 2:
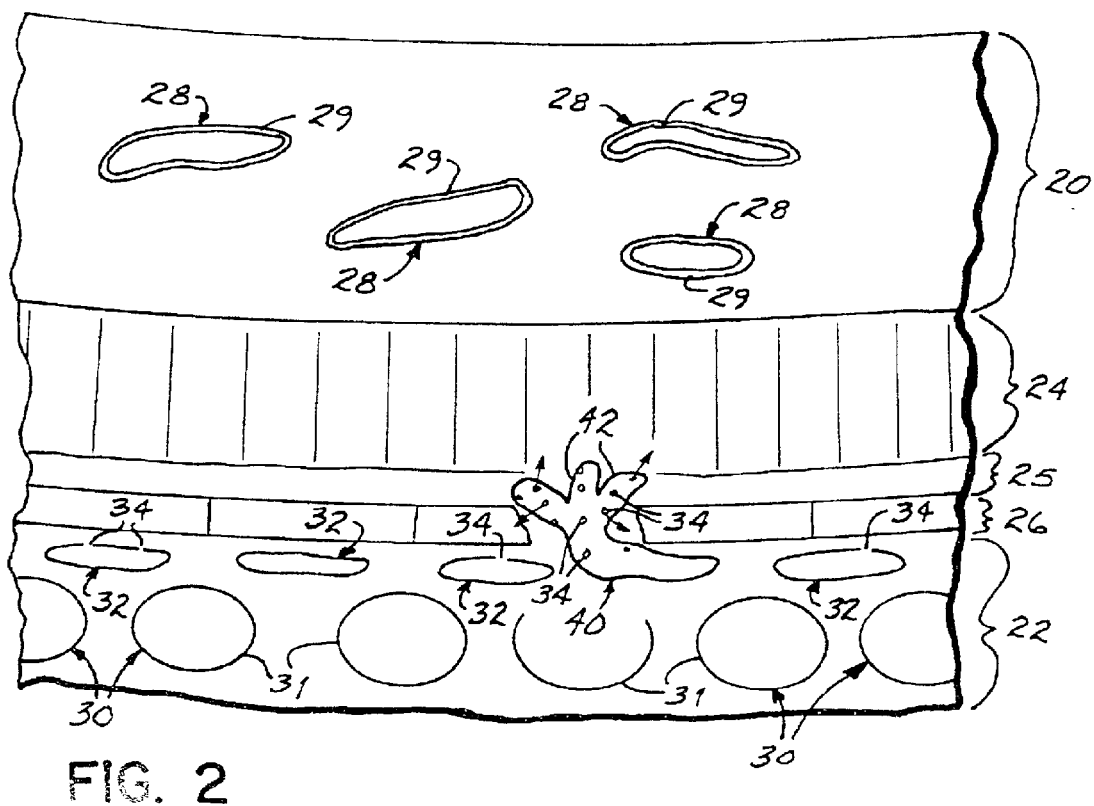
FIG. 2 is an enlarged diagrammatic illustration of the circled area 2 of FIG. 1 showing detailed retinal and choroid structures.

FIG. 2 is a diagrammatic enlargement of the circled area of FIG. 1. Between the retina 20 and the choroid 22 there is an outer segment of photoreceptor cells 24 including rods and cones, a subretinal space 25, and a layer of retinal pigment epithelium (RPE) 26. In a normal adult, retinal blood vessels 28, including capillaries, have walls or membranes 29 that contain no fenestrations or openings. In a normal adult, the large choroidal vessels 30 similarly have walls 31 that contain no fenestrations but the choriocapillaries 32 have walls that contain fenestrations 34. In an adult with macular degeneration (also called age related macular degeneration, AMD), there is either growth of new subretinal blood vessels whose walls or membranes are altered in that they also contain fenestrations, or the RPE cells are lost.

AMD is a pathological, progressive age-related degeneration in the macula lutea 17 of the retina 20. The macula lutea 17 is located in the center of the posterior part of the retina 20 and is the most sensitive portion of the retina 20. In the center of the macula lutea 17 is a depression, the fovea centralis 41, from which rods are absent. About one-tenth inch inside the fovea 41 is the point of entrance of the optic nerve 15 and its central artery. At this point, the retina 20 is incomplete and forms the blind spot.

In exudative AMD, subretinal neovascular tissue 40 develops in the choroid 22. The neovascular tissue 40 penetrates the RPE and subretinal space 25, and extends into the area containing photoreceptor cells 24. The neovascular tissue 40 has membranes or walls 42 that are altered in having fenestrations 34, that permit fluid leakage into spaces surrounding photoreceptor cells 24, the subretinal space 25 and the RPE 26.

Neovascular tissue 40 results in visual impairment because of fluid leakage and accumulation in the spaces surrounding the new vessels. Therapies to prevent AMD are directed to slowing or stopping the formation or proliferation of new vessels in the choroid. Therapies to treat AMD are directed to at least partially damaging or destroy existing neovascular tissue 40, and/or interfering with its function. In either case, leakage of fluid from the new vessels is decreased, and the concomitant scarring and loss of vision is likewise diminished or eliminated. Examples of such methods are disclosed in co-pending U.S. patent application Ser. Nos. 09/235,104 and 09/644,436, each of which is expressly incorporated by reference herein in its entirety.

The invention is directed to a method to prevent AMD in a minimally affected eye or an eye showing early stages of AMD, and to treat and thereby reduce vision loss in an AMD-affected eye, by treating the eye with photodynamic therapy (PDT) in combination with threshold laser coagulation therapy. The therapies may be administered in any sequence, that is, laser coagulation therapy may be administered before or after PDT, or they may be administered essentially simultaneously. The invention is applicable for both exudative and atrophic types of AMD.

The general principles by which PDT and laser coagulation affect AMD are as follows. PDT prevents or alters the function of the neovascular tissue by using low energy light to generate reactive species that damage the tissue. More particularly, the low energy light activates a photoactive or photosensitive agent that has been administered to a patient and which is contained within the new vessel. By targeting low energy light to the area containing the new vessel, the agent in this area is selectively activated. The activated agent generates singlet oxygen and other reactive oxygen radicals such as hydroxyl radicals, which damage the walls of the choriocapillaries and neovascular tissue, leading to an initial vascular thrombus. Threshold laser coagulation therapy slows or halts fluid leakage in and around the new vessels. It uses heat generated by high energy light in a laser to coagulate fluid within and surrounding the new vessels, preventing fluid escape from the leaky vessel wall and further penetration into the surrounding tissues.

PDT is a method for local and selective tissue or cellular destruction by the action of a particular wavelength of low energy light on the photosensitizing agent. The wavelength of light is selected to correspond to the absorbance spectrum of the photosensitizing agent. The agent capable of being photoactivated is administered into the bloodstream of a patient, usually by intravenous injection. The agent is transported in the blood to vessels 28 in the retina 20. Either immediately thereafter, or after an appropriate interval, the agent is activated by directing light of the appropriate wavelength to this specific area. The size of the applied laser may be in the range of about 1 mm to about 9 mm.

The selection of the photosensitive agent depends upon several factors. These factors include the site or sites of tissue distribution requiring treatment, the mechanisms of action of the agents themselves, and their specific optimal absorption wavelengths. For example, tin ethyl etiopurpurin (SnET2), is frequently used as a photosensitive agent. SnET2 has several advantages, such as lower persistence and severity of skin photosensitivity, absorption at longer wavelengths yielding better tissue penetration, a higher extinction coefficient resulting in increased potency and efficiency, ease of synthesis, and ability to be produced in a highly pure form. Protoporphyrin is also a good photosensitizing agent. Protoporphyrin IX is a photoactive compound which is endogenously formed from 5-aminolevulinic acid (ALA) in the biosynthetic pathway of heme. ALA may be applied topically and is metabolized to protoporphyrin, the active photosensitizing agent. Laser irradiation is usually at a wavelength in the range of about 630 nm, or alternatively in the range of 670 nm. ALA may be administered orally in a bolus as an aqueous solution at a concentration of about 60 mg/kg body weight, or intravenously at a concentration of 30 mg/kg body weight. Other photosensitizing agents that may be used include, but are not limited to, benzoporphyrin derivative monoacid tube A (BPD-MA) and mono-l-aspartyl chlorine 6 (NPe6), with absorbance maxima in the range of about 660–690 nm, ATX-106, and indocyanine green (ICG).

Another photosensitive agent that may be used is verteporfin. Verteporfin is a synthetic, chlorin-like porphyrin. After intravenous injection at a dose of about 1–2 mg/kg, it is activated by light at 50 J/cm$^2$ (absorbance peak of drug) from a non-thermal laser (for example, a diode laser) set at an intensity of 600 mW/cm$^2$ and a wavelength of 689 nm. Once activated, it generates singlet oxygen and other reactive oxygen radicals that selectively damage neovascular endothelial cells, and cause thrombus formation due to specific choroidal neovascular occlusion.

Threshold laser coagulation therapy is performed by directing high energy light from any type of laser (for example, argon, krypton, or diode laser) to the macular area, as is known to one skilled in the art. Any wavelength of light (for example, visible light, infrared light) may be used. The energy delivered to create a very light lesion is tested on an extrafoveal area of the fundus. The laser creates multiple coagulation spots surrounding the fovea, and also has beneficial effects on reabsorption of the drusen. Patients having abnormal ocular pathology, such as extrafoveal pigment epithelial detachment, receive additional laser applications directed over these areas.

The size of the applied spots can vary, as can the number of spots applied. In one embodiment, the application spot size is between about 50 μm and about 500 μm. In another embodiment, the application spot size is about 200 μm. In yet another embodiment, the application spot size is greater than 500 μm. Generally, the smaller the spot size, the greater the number of spots that are applied; conversely, the larger the spot size, the fewer the number of spots that are applied. Thus, for smaller sized spots, the number of spots may be between about 50 to about 500 spots. In one embodiment, between about 150 to about 200 spots are administered. For larger sized spots, the number of spots may be between about 5 and about 50 spots. The spots are administered in the macula and adjacent area in a scatter fashion around the fovea. The duration of administration for each spot is between about 0.1 second to about 1 second, with an energy in the range of about 50 mW to about 500 mW.

In the inventive method, both PDT and threshold laser coagulation therapy are administered, but their administration is not restricted to a particular sequence. In one embodiment, PDT is administered and essentially simultaneously with or immediately thereafter laser coagulation therapy is administered. In another embodiment, PDT is administered and laser coagulation therapy is administered in the same treatment session, within a time frame of a few hours. In another embodiment, PDT is administered and laser coagulation therapy is administered after an interval from about one day up to about 90 days. In another embodiment, laser coagulation therapy is administered and essentially simultaneously with or immediately thereafter PDT is administered. In another embodiment, laser coagulation therapy is administered and PDT is administered in the same treatment session, within a time frame of a few hours. In another embodiment, laser coagulation therapy is administered and PDT is administered after an interval from about one day up to about 90 days.

In one embodiment, after administering the photosensitive agent (verteporfin, protoporphyrin, SnET2, NPe6, ATX-106, ICG, etc.), the patient is treated using a laser to administer low energy levels of light at a wavelength appropriate to activate the photosensitive agent. Threshold laser coagulation therapy is then essentially simultaneously or concomitantly initiated. Essentially simultaneously with includes administration of both high energy and low energy light within the same treatment session. Concomitant therapy includes administration either immediately thereafter or within a few hours, within 24 hours, or after an interval from about one day to ninety days.

In another embodiment, the patient is treated with threshold laser coagulation therapy, and is thereafter treated with PDT. The photosensitive agent may be administered either before or after laser coagulation treatment, depending upon a variety of factors such as the specific photosensitive agent used, the specific treatment protocol, etc. PDT is then simultaneously or concomitantly initiated, as described above.

Factors such as patient comfort, tolerance to treatment, and convenience may be factored into selecting the appropriate treatment regime. Exudates disappear within eight to ten weeks post treatment. The macula initially becomes dry, then improves and stabilizes after about three to six months post-treatment.

Patients who have been administered a photoactive agent are cautioned to avoid sunlight exposure for an appropriate period of time to prevent skin hypersensitivity. This period of time may vary, but is usually between five days and thirty days. During this time, the patient should minimize any time outdoors, and should take extra precautions when it is necessary to be outdoors. For patients who normally enjoy outdoor activities, live in a temperate climate, and/or desire to carry out their daily routines, such restrictions may be quite burdensome.

Therefore, in one embodiment of the invention, a patient who has been administered a photosensitive agent for PDT undergoes plasmaphoresis to remove or decrease the concentration of the photosensitive agent in the circulation. Another benefit of plasmaphoresis is that it reduces excessive cholesterol, low density lipoproteins, and other blood components that might aggravate AMD, therefore plasmaphoresis may be an advantageous treatment to patients with AMD at times other than following PDT.

Generally, plasmaphoresis involves the withdrawal, purification, and reinfusion of the purified blood back into the patient from whom it was withdrawn. It involves minimal patient discomfort, little patient time (two to three hours), and minimal safety risk, since the patient is reinfused with his or her own blood. The technical aspects of plasmaphoresis are known to one skilled in the art.

In one embodiment, the patient has an intravenous line in place for administration of the photosensitive agent and undergoes PDT. Thereafter, a second intravenous line is started and the patient undergoes plasmaphoresis; blood is withdrawn from one intravenous line and flows into an apparatus that separates the liquid plasma from the cellular components. The plasma then flows through a separating and/or filtering system, for example, an ion-exchange or other type of resin, that removes undesired substances such as the photosensitive agent. The patient's now filtered plasma is reinfused via the other intravenous line. Plasmaphoresis may be conducted immediately or shortly after PDT. Plasmaphoresis may also be conducted at a later time, such as within twenty-four hours of PDT, during which time the indwelling intravenous line may be left in place with suitable protections, as is known to one skilled in the art.

Eighteen patients ranging in age from 50–80 years of age, and either previously diagnosed with AMD or with early stage AMD have been treated using the inventive method. All of these patients experienced at least some loss of vision pre-treatment.

For PDT, verteporfin was the photosensitive agent and was administered intravenously at a dose of 1–2 mg/kg. Verteporfin was activated using a coherent laser with the red beam (krypton) at a wavelength of 640 nm. For laser coagulation therapy, the spot size was 200 $\mu$m and the duration was 0.4 seconds. The number of spots applied was between 150 and 350. The interval between PDT and laser coagulation therapy was 5 minutes to 24 hours.

Improved visual acuity was achieved in fifty percent (9/18) of these patients post-treatment within six to eight weeks post-treatment, as assessed by accurate reading of a standard vision chart. This is a dramatic improvement over the previously described results in patients treated with PDT alone, in which over 60% of the patients lost some vision but less than 15 letters, 40% of the patients lost more than 15 letters, and only 16% of the patients showed improved vision.

Of the eighteen patients treated with the inventive method, the vision in the remaining fifty percent (9/18) of the patients remained stable over six to nine months, assessed by no further loss of visual acuity.

Beneficially, in the entire patient population treated with the inventive method, the incidence of the need for retreatment has been zero. Also advantageously, there have been no cases of laser-induced neovascularizations in patients receiving the inventive treatment.

The inventive therapy prevents new vessels (subretinal neovascularization) from forming at the site of treatment, which occur when laser coagulation therapy is administered without PDT. The inventive therapy also prevents recurrence of new vessel formation, a problem associated with separate PDT therapy.

The inventive treatment method has been used successfully to prevent AMD in patients who have diffuse occult lesions (a form of AMD), early stages of AMD (drusen, pigment clumps, etc.), and a combination of pigment with epithelial detachment and neovascular membrane.

The inventive method thus treats AMD, and further reduces or eliminates the need for retreatment. It also prevents or alleviates onset, and slows the progression, of AMD without inducing further growth of new vessels from the laser treatment itself.

It should be understood that the embodiments of the present invention shown and described in the specification are only preferred embodiments of the inventor who is skilled in the art and are not limiting in any way. For example, the inventive method may be used in conjunction with administration of other agents such as anti-angiogenic agents (e.g., systemic or intraocular), anti-proliferative agents, and/or with steroids (e.g., subconjunctival depot steroid therapy). Therefore, various changes, modifications or alterations to these embodiments may be made or resorted to without departing from the spirit of the invention and the scope of the following claims.

What is claimed is:

1. A method to prevent, delay or alleviate macular degeneration characterized by fluid leakage from new blood vessel proliferation in the macula of a patient comprising
providing an effective amount of a photosensitive agent to the vessels and thereafter activating said agent with a low energy light to damage said vessels, and
directing to the macula a high energy light sufficient to generate heat to coagulate said fluid, to reduce fluid accumulation, thereby controlling both vessel proliferation and fluid leakage.

2. The method of claim 1 wherein the low energy light is applied before the high energy light.

3. The method of claim 1 wherein the high energy light is applied before the low energy light.

4. The method of claim 1 wherein the photosensitive agent is selected from the group consisting of verteporfin, protoporphyrin, SnET2, NPe6, ATX-106, ICG, and BPD-MA.

5. The method of claim 1 wherein the photosensitive agent is verteporfin activated at about 50 $J/cm^2$ at an intensity of about 600 $mW/cm^2$.

6. The method of claim 1 wherein the high energy light is from an argon or diode laser.

7. The method of claim 1 wherein the high energy light is applied in spots of sizes in the range of about 50 $\mu$m to about 500 $\mu$m.

8. The method of claim 7 wherein between about 50 to about 500 spots are administered.

9. The method of claim 1 in conjunction with administration of other agents selected from the group consisting of anti-angiogenic agents, anti-proliferative agents, steroids, and combinations thereof.

10. The method of claim 1 in conjunction with administration of an anti-angiogenic agent.

11. The method of claim 10 where the anti-angiogenic agent is administered systemically or intraocularly.

12. The method of claim 1 in conjunction with administration of an anti-proliferative agent.

13. The method of claim 1 in conjunction with administration of a steroid.

14. A method to improve visual acuity in an eye of a patient with macular degeneration characterized by fluid leakage from new blood vessels in the macula comprising providing an effective amount of a photosensitive agent to the vessels and thereafter activating said agent with low energy light to damage said vessels, and directing to the macula high energy light sufficient to generate heat to coagulate fluid to reduce leakage from the vessels.

15. The method of claim 14 wherein the low energy light is applied before the high energy light.

16. The method of claim 14 wherein the high energy light is applied before the low energy light.

17. The method of claim 14 wherein the photosensitive agent is selected from the group consisting of verteporfin, protoporphyrin, SnET2, NPe6, ATX-106, ICG, and BPD-MA.

18. The method of claim 14 wherein the photosensitive agent is verteporfin activated at about 50 $J/cm^2$ at an intensity of about 600 $mW/cm^2$.

19. The method of claim 14 wherein the high energy light is from an argon or diode laser.

20. The method of claim 14 wherein the high energy light is applied in spots of size in the range of about 50 $\mu$m to about 500 $\mu$m.

21. The method of claim 20 wherein between about 50 to about 500 spots are administered.

22. The method of claim 14 in conjunction with administration of other agents selected from the group consisting of anti-angiogenic agents, anti-proliferative agents, steroids, and combinations thereof.

23. The method of claim 14 in conjunction with administration of an anti-angiogenic agent.

24. The method of claim 23 where the anti-angiogenic agent is administered systemically or intraocularly.

25. The method of claim 14 in conjunction with administration of an anti-proliferative agent.

26. The method of claim 14 in conjunction with administration of a steroid.

* * * * *

UNITED STATES PATENT AND TRADEMARK OFFICE
CERTIFICATE OF CORRECTION

PATENT NO. : 6,936,043 B2 Page 1 of 1
DATED : August 30, 2005
INVENTOR(S) : Peyman It is certified that error appears in the above-identified patent and that said Letters Patent is hereby corrected as shown below:

Title page,
Item [56], References Cited, OTHER PUBLICATIONS,
"The Choroidal Neovascularization..." reference, "...Prevention Trail Group" should be
-- ...Prevention Trial Group --; and
delete the second occurrence of the "The Choroidal Neovascularization Prevention Trail Group..." reference.

Signed and Sealed this

Fourteenth Day of February, 2006

JON W. DUDAS
*Director of the United States Patent and Trademark Office*